US011865065B2

(12) United States Patent
Zack et al.

(10) Patent No.: US 11,865,065 B2
(45) Date of Patent: Jan. 9, 2024

(54) FOLDING SAUNA ENCLOSURE

(71) Applicant: Sunlighten, Inc., Overland Park, KS (US)

(72) Inventors: Aaron Michael Zack, Overland Park, KS (US); Brian Franson, Kansas City, MO (US); Brett Pearson, Kansas City, MO (US); Jonathon Kemnitzer, Kansas City, MO (US)

(73) Assignee: Sunlighten, Inc., Overland Park, KS (US)

( * ) Notice: Subject to any disclaimer, the term of this patent is extended or adjusted under 35 U.S.C. 154(b) by 391 days.

(21) Appl. No.: 17/344,601

(22) Filed: Jun. 10, 2021

(65) Prior Publication Data

US 2021/0386620 A1   Dec. 16, 2021

Related U.S. Application Data

(60) Provisional application No. 63/037,915, filed on Jun. 11, 2020.

(51) Int. Cl.
*A61H 33/06* (2006.01)
*A61N 5/06* (2006.01)

(52) U.S. Cl.
CPC ......... *A61H 33/066* (2013.01); *A61H 33/063* (2013.01); *A61N 5/0625* (2013.01); *A61H 2033/061* (2013.01); *A61H 2201/10* (2013.01); *A61N 2005/066* (2013.01); *A61N 2005/0632* (2013.01); *A61N 2005/0633* (2013.01); *A61N 2005/0634* (2013.01); *A61N 2005/0637* (2013.01); *A61N 2005/0658* (2013.01); *A61N 2005/0659* (2013.01)

(58) Field of Classification Search
CPC .......... A61H 2201/10; A61H 2033/061; A61H 33/063; A61H 33/066; A61N 5/06; A61N 5/0625; A61N 2005/0632; A61N 2005/0633; A61N 2005/0634; A61N 2005/0637; A61N 2005/0658; A61N 2005/0659; A61N 2005/066
See application file for complete search history.

(56) References Cited

U.S. PATENT DOCUMENTS 6,549,809 B2   4/2003   Ono
8,588,593 B2   11/2013  Zack et al.
(Continued)

FOREIGN PATENT DOCUMENTS

CN   202875692 U   4/2013
CN   206006194 U   3/2017
JP   H11239624 A   9/1999

*Primary Examiner* — Kaitlyn E Smith
*Assistant Examiner* — Bradford C. Blaise
(74) *Attorney, Agent, or Firm* — AVEK IP, LLC; Kent R. Erickson

(57) ABSTRACT

A portable, personal therapy chamber for provision of radiation therapy. The therapy chamber includes a pair of telescopically positionable units that are lightweight and easily portable by a single user. The therapy chamber is configured for use by a single person lying generally prone on a surface. The units are formed from a plurality of pivotably coupled panels that are foldable in a first direction to a rolled up, tube-like storage configuration and unfoldable in a second direction to an arched formation or use configuration. The units, in the use configuration, are disposed to overlie the user and include a plurality of emitters that direct infrared energy toward the user's body.

20 Claims, 9 Drawing Sheets

(56) References Cited

U.S. PATENT DOCUMENTS

| | | | |
|---|---|---|---|
| 8,676,044 | B2 | 3/2014 | O'Keeffe et al. |
| 8,737,827 | B2 | 5/2014 | Zack et al. |
| 9,744,098 | B2 | 8/2017 | O'Keeffe et al. |
| 10,376,442 | B2 | 8/2019 | O'Keeffe et al. |
| 10,616,955 | B1 | 4/2020 | Zack |
| 10,874,586 | B2 | 12/2020 | O'Keeffe et al. |
| 11,207,542 | B1 | 12/2021 | Ruzicka |
| 11,638,659 | B2 | 5/2023 | Dijkstra |
| 2004/0093043 | A1 | 5/2004 | Edel et al. |
| 2016/0081500 | A1 | 3/2016 | Bradshaw |
| 2019/0358120 | A1 | 11/2019 | O'Keeffe et al. |
| 2020/0008996 | A1 | 1/2020 | Zack |
| 2020/0069516 | A1 | 3/2020 | Zack et al. |
| 2021/0113429 | A1 | 4/2021 | O'Keeffe et al. |
| 2021/0137781 | A1 | 5/2021 | Zack et al. |

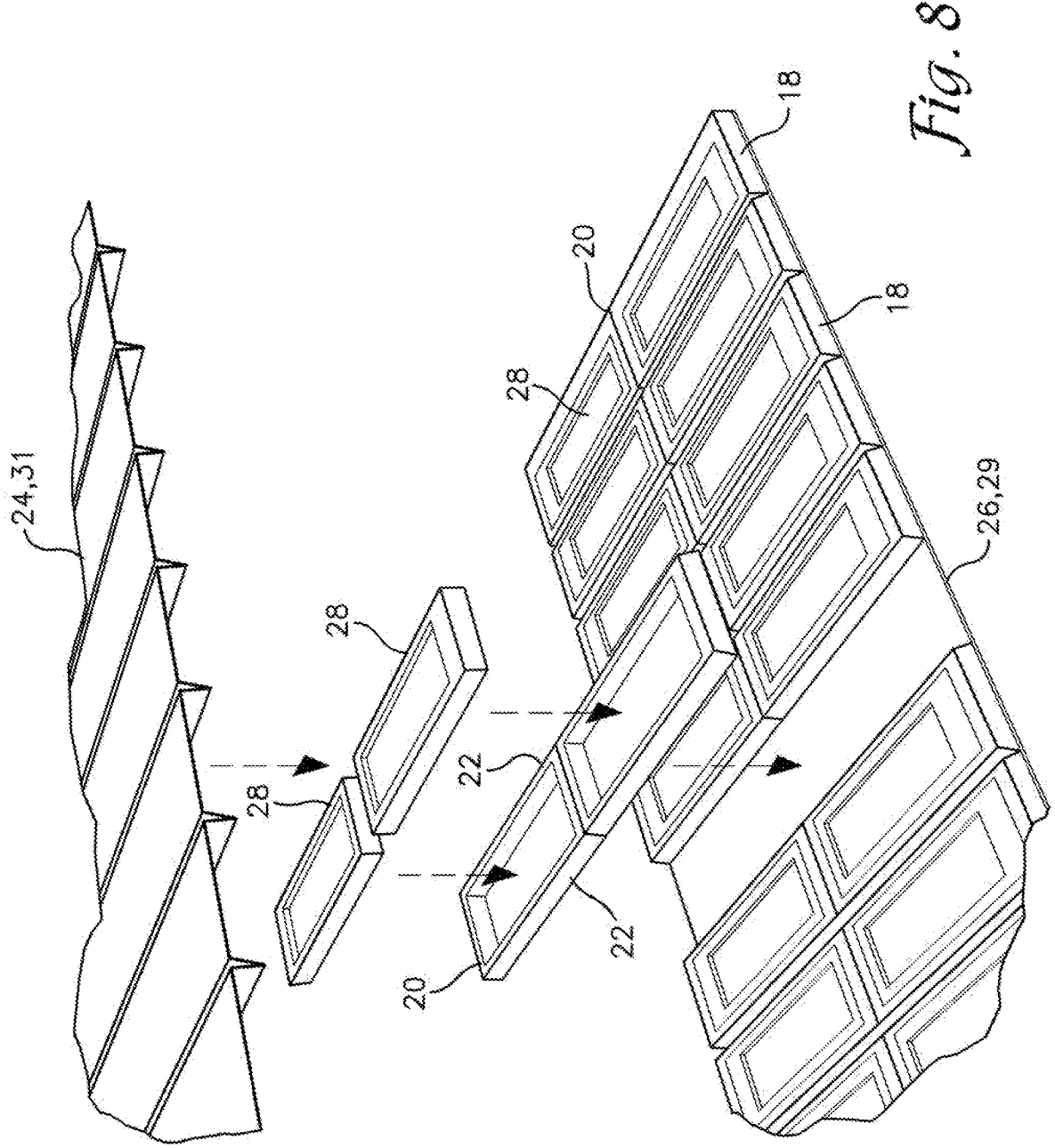

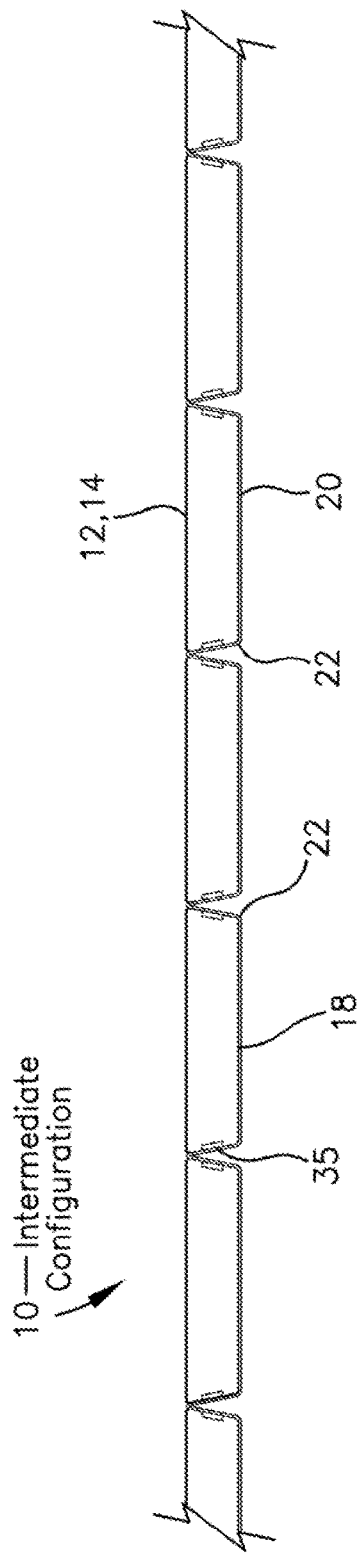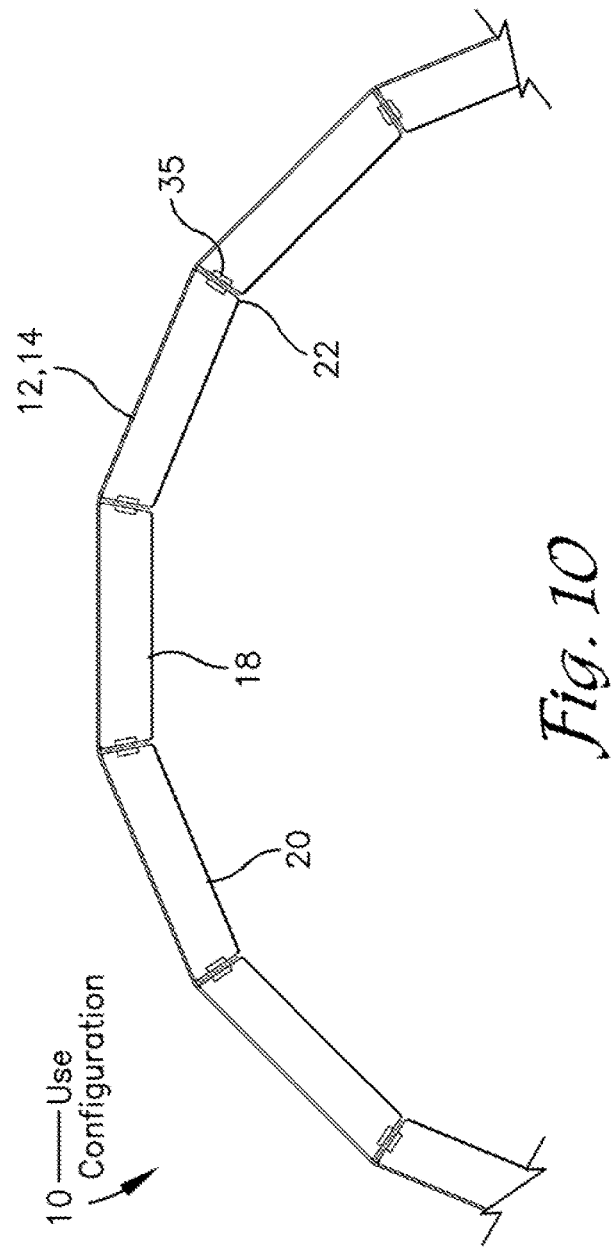

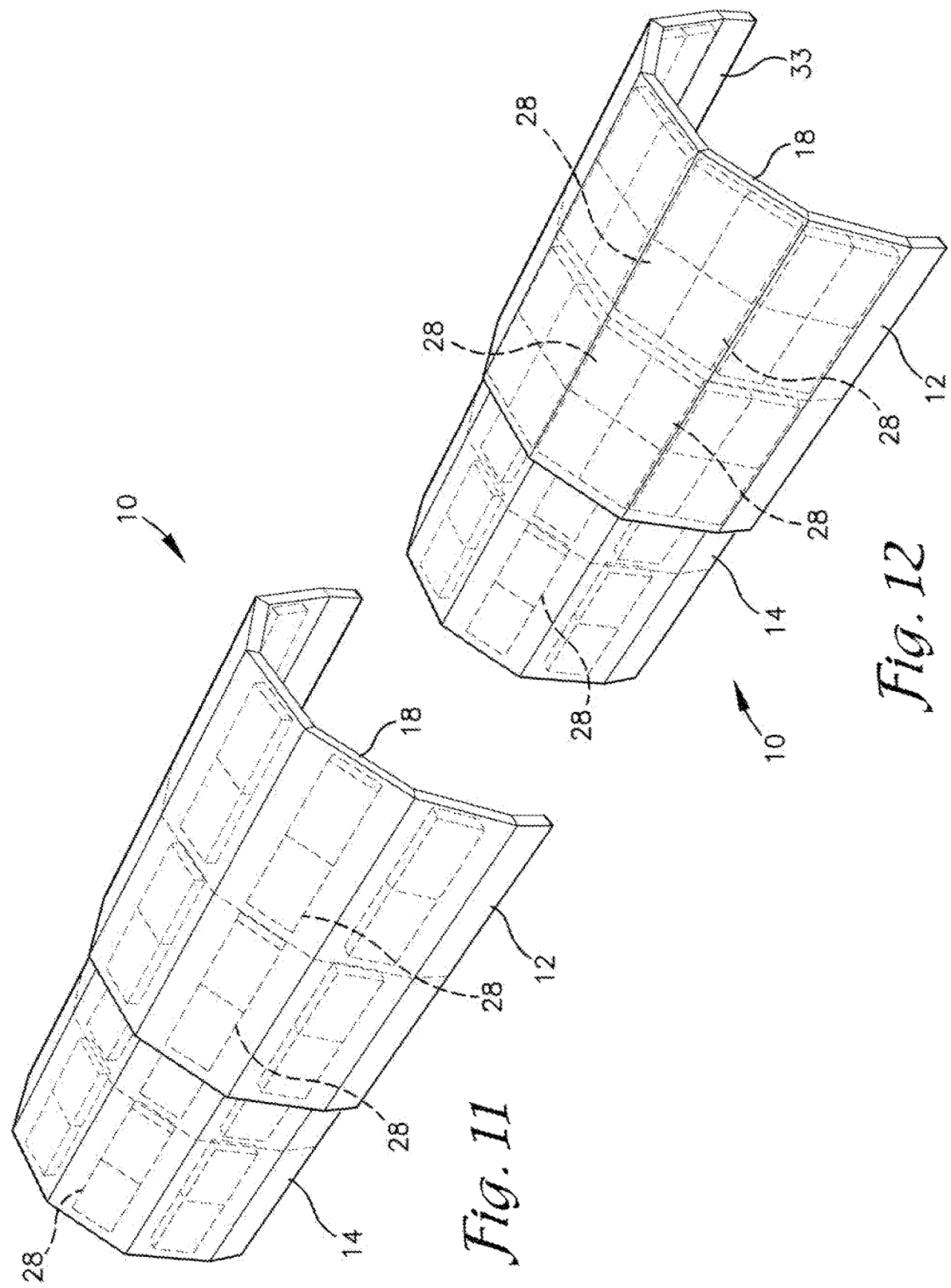

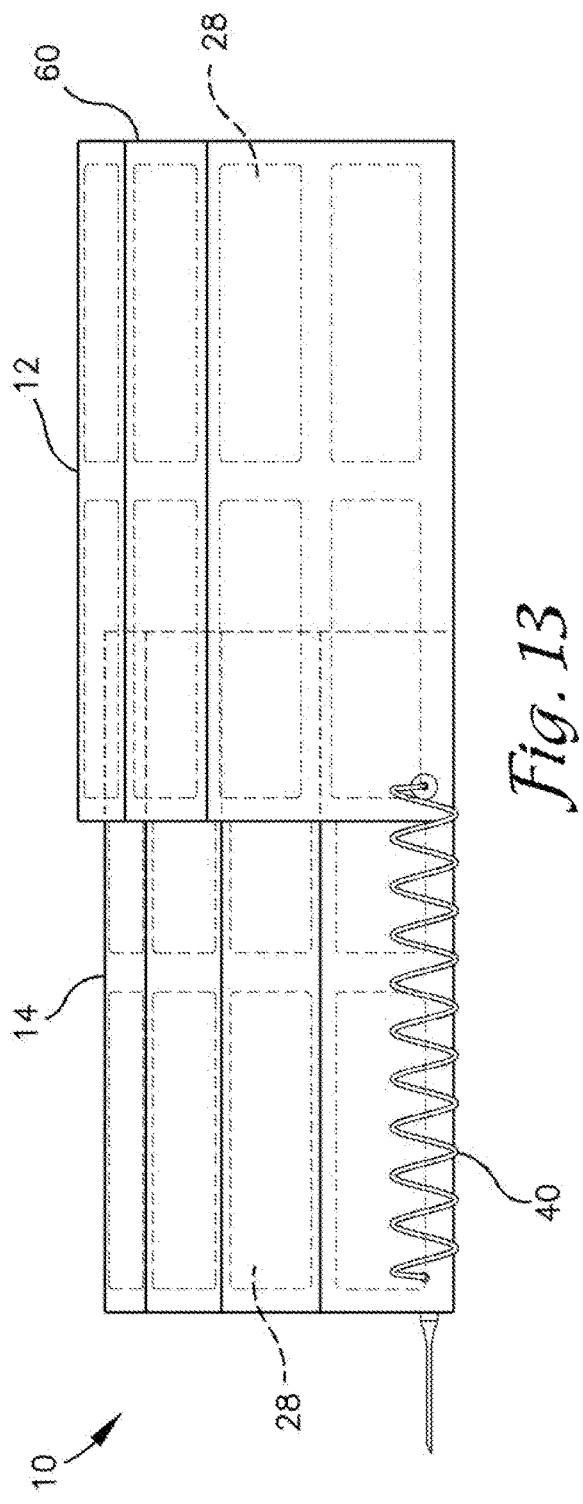
Fig. 13
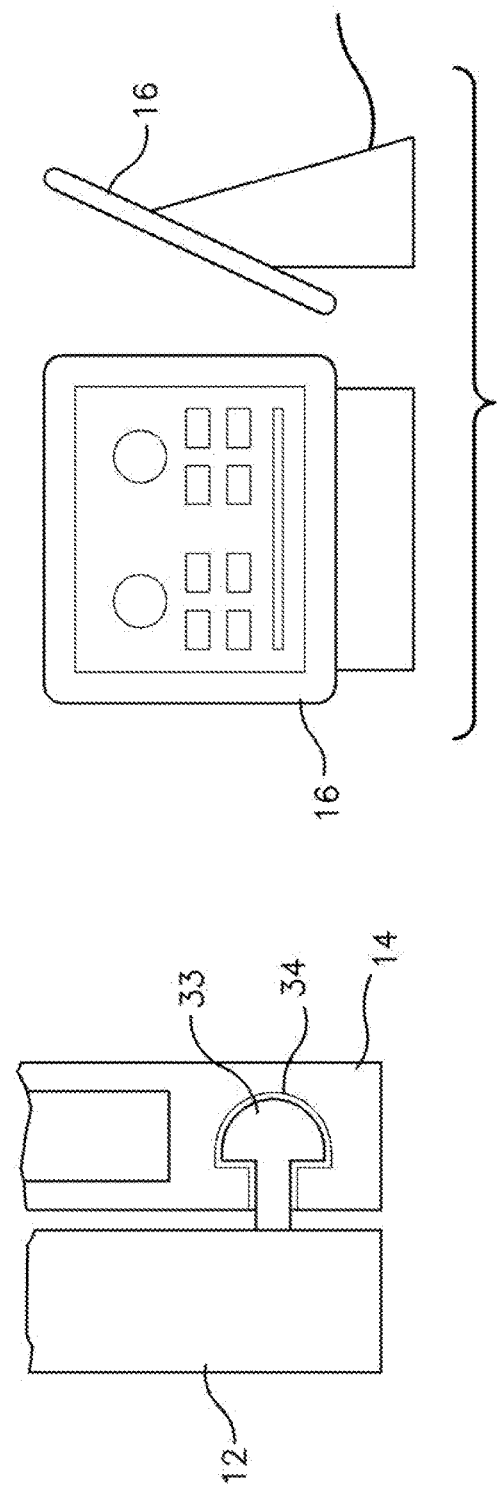
Fig. 14
Fig. 15

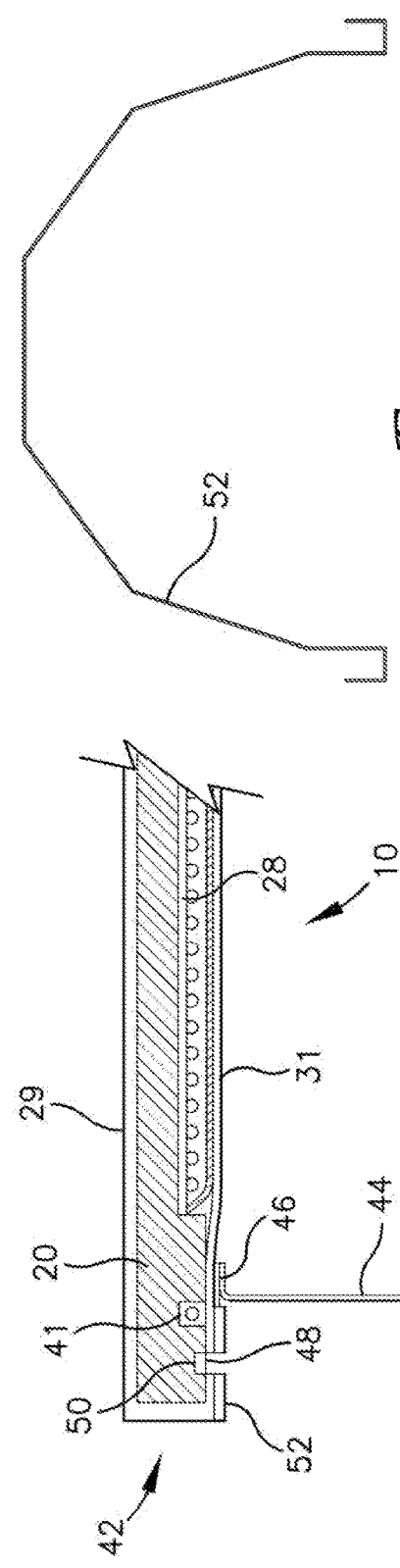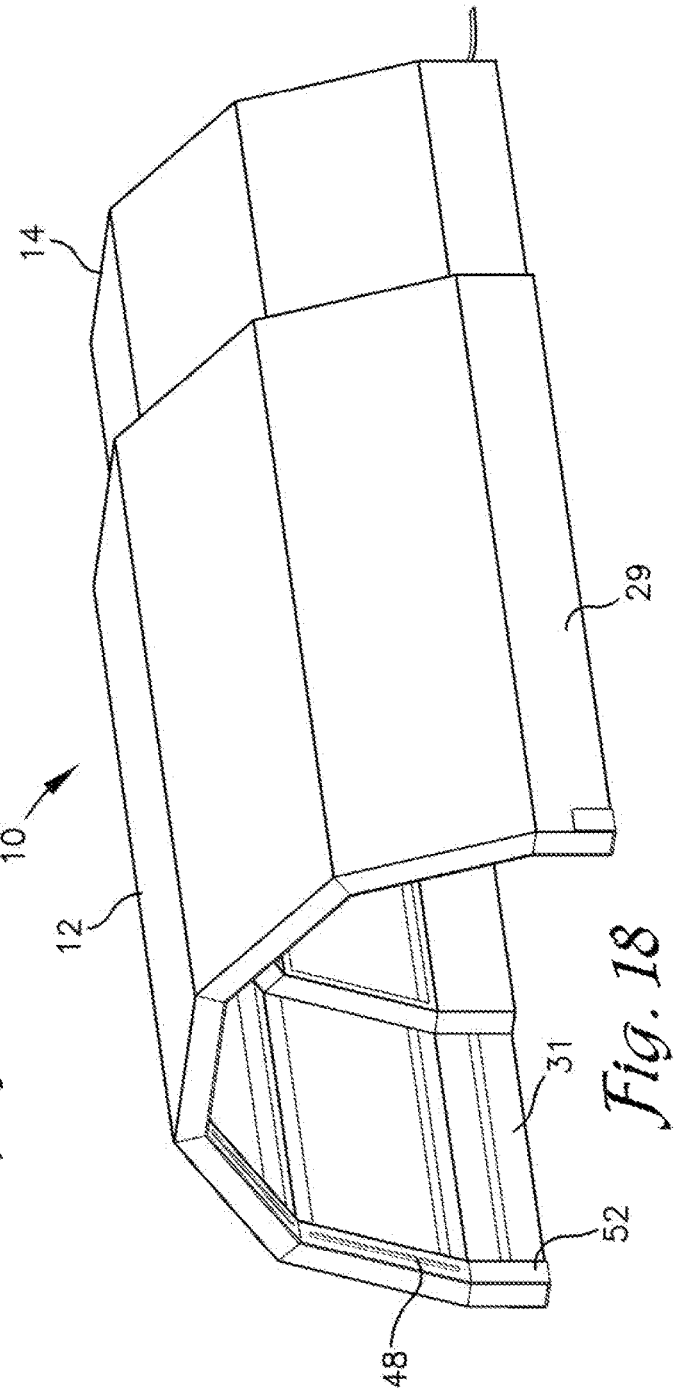

FOLDING SAUNA ENCLOSURE

CROSS-REFERENCE TO RELATED APPLICATIONS

This application claims the benefit of U.S. Provisional Patent Application No. 63/037,915, filed Jun. 11, 2020 the disclosure of which is hereby incorporated herein in its entirety by reference.

BACKGROUND

Dry saunas are increasingly popular as personal accessories in modern homes to deliver on-demand healthful dry heat therapy. These saunas are typically relatively small in size (housing from 1-6 individuals) and are constructed in a user's home as a semi-permanent, non-portable structure.

Personal saunas and therapy units have also been developed that are intended for use by one person at a time. Many such saunas are designed to be easily moveable for storage or transport to other locations. These personal saunas are thus typically relatively compact so as to reduce the overall footprint of the unit during both use and storage and to ease handling by the user. For example, U.S. Pat. No. 10,616,955 to Zack and U.S. Pat. No. 6,549,809 to Ono describe saunas and health appliances configured for use by a single user. FIG. 1 depicts a similar prior art personal sauna unit 1 having a pair of telescoping sections that can be disposed on a surface to form a chamber within which a single user may be positioned to receive a therapy and which can be easily telescopically moved and/or stood on end for storage in a relatively compact space.

Chromotherapy or light therapy is also a popular addition to the personal health regimen of many people. Many psychological, physical, emotional, and spiritual benefits are thought to stem from exposure to various colors or wavelengths of light in the visible spectrum. For example, red light may provide the user with the feeling of being energized, green light may aid healing processes, and blue light may aid mental relaxation among other potential benefits.

Additionally, it has been found that exposure of the human body to near-infrared radiation may provide health benefits, such as increased blood circulation, reduced inflammation, increased healing rates, and/or pain relief, among other benefits. Near-infrared treatment may be employed to activate photo-reactive medications or substances that are ingested, injected, applied topically, or otherwise provided to a user's body.

Devices, such as dry saunas are known in the art for provision of infrared radiation to a user, but such devices generally limit or eliminate near-infrared radiation in the provided treatment spectrum. Known devices configured to provide near-infrared radiation treatments are large, very expensive beds or chambers that are relatively inaccessible to the common consumer due to cost and/or space requirements. Other devices include small handheld wands that can only treat very small portions of the user's body at any given time.

SUMMARY

Exemplary embodiments are defined by the claims below, not this summary. A high-level overview of various aspects thereof is provided here to introduce a selection of concepts that are further described in the Detailed-Description section below. This summary is not intended to identify key features or essential features of the claimed subject matter, nor is it intended to be used in isolation to determine the scope of the claimed subject matter. In brief, this disclosure describes, among other things, a personal therapy unit that is foldable into a highly transportable and/or storable form.

In one embodiment, the personal therapy chamber includes an upper unit and a lower unit each having a generally half-cylindrical form when in a use configuration. The lower unit is sized with a radius that is just smaller than that of the upper unit such that the lower unit can be moved relative to the upper unit in a telescoping manner. The units are configured to overlie a user that is lying in a generally prone position on a surface with the head of the user extending beyond a terminal end of the upper unit and the remainder of the user's body being enclosed between the units and the surface. A foot panel may be provided and coupled to a terminal end of the lower unit to enclose the terminal end. A pad or mat may also be provided that can be placed on the surface beneath the user and the units.

Each of the units comprises a plurality of generally elongate, rectangular, planar panels disposed side-by-side and pivotably coupled along their adjacent longitudinal edges. Each of the panels includes a frame outlining the panel and supporting one or more emitters. Pivotable couplings between the frames enable the unit to be positioned and moved between a use configuration, an intermediate configuration, and a storage configuration. When pivoted in a first direction, the panels can be rolled up or folded into the storage configuration which comprises a tube-like form. When pivoted in an opposite second direction to the use configuration, abutment of longitudinal edges of the panels defines a limit to the extent of the pivotal movement in the second direction and places the panels in an arcuate or partial cylindrical shell-like form.

The emitters may comprise a plurality of infrared- and/or visible-light-emitting elements disposed in the frames of the head-end and lower units to emit infrared radiation and/or visible light that is directed toward a user's body. The infrared energy from the emitters may be provided in the near-, mid-, and/or far-infrared spectrums. The foot panel and the pad may also be configured to include one or more emitters.

The personal therapy chamber includes a control unit through which the user may control the emitters independently or in groups. The control unit may be configured to detect an overlap between the head-end and lower units and/or to control one or more emitters of the upper unit within the overlap to reduce or eliminate heating of the exterior surface of the lower unit.

DESCRIPTION OF THE DRAWINGS

Illustrative embodiments are described in detail below with reference to the attached drawing figures, and wherein:

FIG. 8 is an enlarged partially exploded perspective view of one unit of a personal therapy unit depicted in accordance with an exemplary embodiment;

FIG. 9 is a partial end elevational view of one unit of a personal therapy chamber in the intermediate configuration depicted in accordance with an exemplary embodiment;

FIG. 10 is a partial end elevational view of one unit of a personal therapy chamber in the use configuration depicted in accordance with an exemplary embodiment;

FIG. 11 is a schematic, perspective view of a personal therapy chamber with a single row of emitters disposed along the length of each panel forming the units of the personal therapy chamber depicted in accordance with an exemplary embodiment;

FIG. 12 is a schematic, perspective view of a personal therapy chamber with two rows of emitters disposed along the length of each panel forming an upper unit of the personal therapy device depicted in accordance with an exemplary embodiment;

FIG. 13 is a side elevational view of a personal therapy device showing an overlap between an upper unit and a lower unit of the unit depicted in accordance with an exemplary embodiment;

FIG. 14 is an end elevational view of a rail and track system that may be employed to assist telescopic movement and engagement between the upper and lower units of the personal therapy chamber;

FIG. 15 is a front and side elevational view of a controller useable with a personal therapy chamber depicted in accordance with an exemplary embodiment;

FIG. 16 is a longitudinal, cross-sectional view of a terminal end of an upper unit of a portable therapy chamber depicted in accordance with an exemplary embodiment;

FIG. 17 is an end view of a support useable with a portable therapy chamber depicted in accordance with an exemplary embodiment;

FIG. 18 is a perspective view of a portable therapy chamber with the support member of FIG. 17 installed thereon in accordance with an exemplary embodiment.

DETAILED DESCRIPTION

Figure 3:
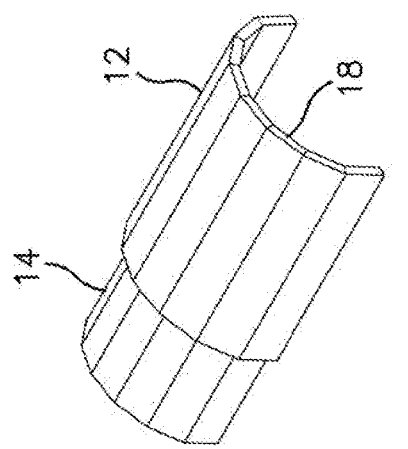
FIG. 3 is a perspective view of two units like that depicted in FIG. 2 disposed in a telescoping fashion to form a personal therapy chamber in accordance with an exemplary embodiment.
Figure 2:
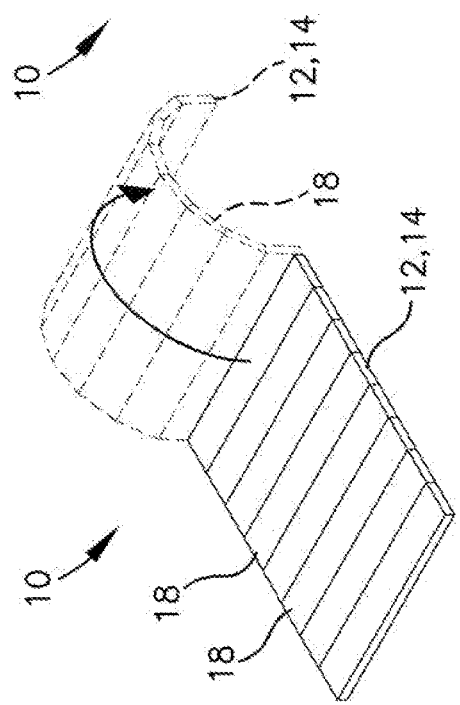
FIG. 2 is perspective view of one unit of a folding personal therapy chamber depicting a planar intermediate configuration in bold lines and a use configuration in phantom lines in accordance with exemplary embodiment.
Figure 1:
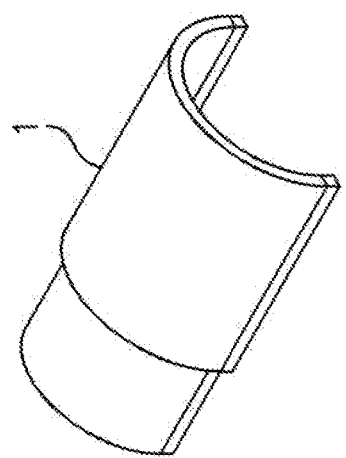
FIG. 1 is a perspective view of a prior art personal sauna device.

The subject matter of select exemplary embodiments is described with specificity herein to meet statutory requirements. But the description itself is not intended to necessarily limit the scope of the claims. Rather, the claimed subject matter might be embodied in other ways to include different components, steps, or combinations thereof similar to the ones described in this document, in conjunction with other present or future technologies. Terms should not be interpreted as implying any particular order among or between various steps herein disclosed unless and except when the order of individual steps is explicitly described. The terms "about" or "approximately" or "substantially" as used herein denote deviations from the exact value by +−10%, preferably by +/−5% and/or deviations in the form of changes that are insignificant to the function.

With reference to FIGS. 2-3 and 6-10, a personal therapy chamber 10 is described in accordance with an exemplary embodiment. The therapy chamber 10 comprises a head-end or upper unit 12 and a foot-end or lower unit 14, and a control unit 16. The upper and lower units 12, 14 are each comprised of a plurality of generally rectangular panels 18 that are hingedly or pivotably coupled along their longitudinal or long edges. Each of the panels 18 includes a frame member 20 that outlines or forms a perimeter of the panel 18 and may or may not include a wall spanning across and closing off an interior of the frame member 20. The frame members 20 are preferably constructed from a light-weight material to reduce the overall weight of the therapy chamber 10. For example, the frame members 20 may be constructed from an aluminum alloy or other metal alloy or may comprise a plastic material, such as expanded polypropylene (EPP), polyethylene terephthalate (PET) or similar material which may be blown or include a blowing agent to decrease its density and weight, among a variety of other materials.

The frame member 20 has a thickness sufficient to provide the longitudinal edges with a generally planar side face 22. The side face 22 is positioned on a slight angle, i.e. between about 2° and about 20°, relative to the plane of the panel 18 such that an interior face 24 of the panel 18 has a slightly smaller width than an exterior face 26 of the panel 18. Accordingly, when the side faces 22 of adjacent panels 18 are abutted, the panels 18 are positioned at an angle relative to one another.

Figure 7:
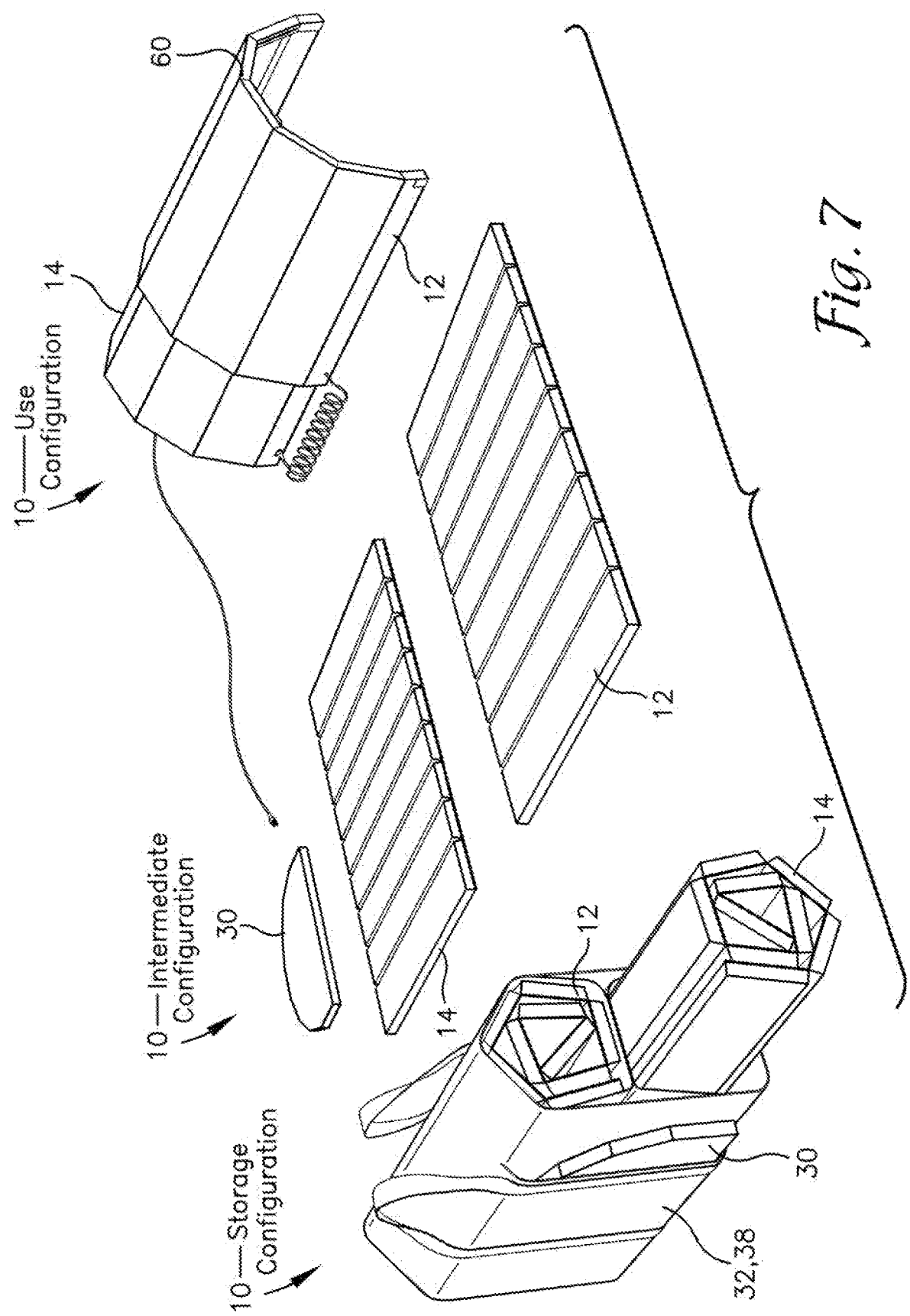
FIG. 7 is perspective view showing, from left to right, a personal therapy chamber in a storage configuration, an intermediate configuration, and a use configuration depicted in accordance with an exemplary embodiment.

Adjacent ones of the panels 18 are pivotably or hingedly coupled together along their longitudinal edges and generally at or adjacent to their exterior faces 26. In one embodiment, a sheet 29 comprised of one or more fabrics or textile materials is disposed on the exterior faces 26 of the panels 18 and spanning between the panels 18 to form the pivotable coupling therebetween in a manner similar to what is commonly known in the art as a living hinge. Any of a variety and/or combination of fabrics, textiles, plastics, rubbers, or other materials may be employed. One such material may be at least partially comprised of a fabric formed from an infrared textile such as CELLIANT polyester, nylon, or viscos fabrics from Hologenix, LLC of Pacific Palisades, Calif. or carbonized bamboo filament alone or in combination with other fibers. Other embodiments may incorporate mechanical hinges or other types of pivotable joints or connections. As such, when pivoted relative to one another in a first direction, the panels have a greater degree of freedom or greater range of motion which allows the unit 12, 14 to generally be rolled up or folded onto itself into a tube-like form identified herein as the storage configuration, as depicted in FIG. 7. The units 12, 14 might also simply be folded onto itself, such as in half, to take a planar or flat form which may aid storage, transport, and/or packaging thereof.

From the storage configuration, the units 12, 14 may be unrolled or the panels 18 pivoted in an opposite second direction to the intermediate configuration in which the panels 18 are generally aligned within a single plane, as depicted in FIGS. 7 and 9. Pivoting of the panels 18 in the second direction continues until the side faces 22 come into abutment and the unit 12, 14 assumes the use configuration, as depicted in FIGS. 7 and 10.

In the use configuration, the angle of the panels 18 relative to one another is such that the unit 12, 14 takes an arcuate or arched formation when viewed from an end thereof. The arched formation is configured to provide an interior radial dimension sufficient to receive at least a portion of a human user's body within the arched formation and between the arched formation and a surface on which the chamber 10 is disposed. Preferably the arched formation of the upper unit 12 has dimensions sufficient to receive at least a portion of the human user's torso and the lower unit 14 has dimensions sufficient to receive the user's legs therein.

The number, width, and angles of the panels 18 relative to one another are configured to maintain the arched form without reinforcement by other means. In other words, the units 12, 14 maintain the arched use configuration via forces applied by gravity and abutment of the side faces 22 of the panels 18. In one embodiment, a plurality of releasable retention elements 35 are disposed in the side faces 22 of the frame members 20 to aid retention of the upper or lower unit 12, 14 in the use configuration with or without the aid of forces applied by gravity. The retention elements 35 may comprise magnets, hook-and-loop fasteners, snaps, clasps, or other mechanical or non-mechanical engagements that aid retention of the upper and lower units 12, 14 in the use configuration.

In yet another embodiment, an arcuate support member 52 is provided and is configured for installation on the upper or lower unit 12, 14 when in the use configuration to aid retention of the unit 12, 14 in such configuration. The support member 52 may comprise a strip of resilient or rigid material, such as an aluminum, a plastic, or the like, formed in an arc with ends configured to engage lateral edges of the respective upper or lower unit 12, 14. As depicted in FIGS. 17 and 18, the ends of the support member 52 may be hooked to wrap around the lateral edges of the upper or lower unit 12, 14 and/or may include another feature or element configured to releasably engage the upper or lower unit 12, 14. The support member 52 may be formed to mimic the facets and/or arc of an inner surface of the upper or lower unit 12, 14 on which the support member 52 is installed or may be provided with another profile. The support member 52 might alternatively be configured for installation on an exterior surface of the upper or lower unit 12, 14 or on both the interior and exterior surfaces thereof among other configurations.

Figure 6:
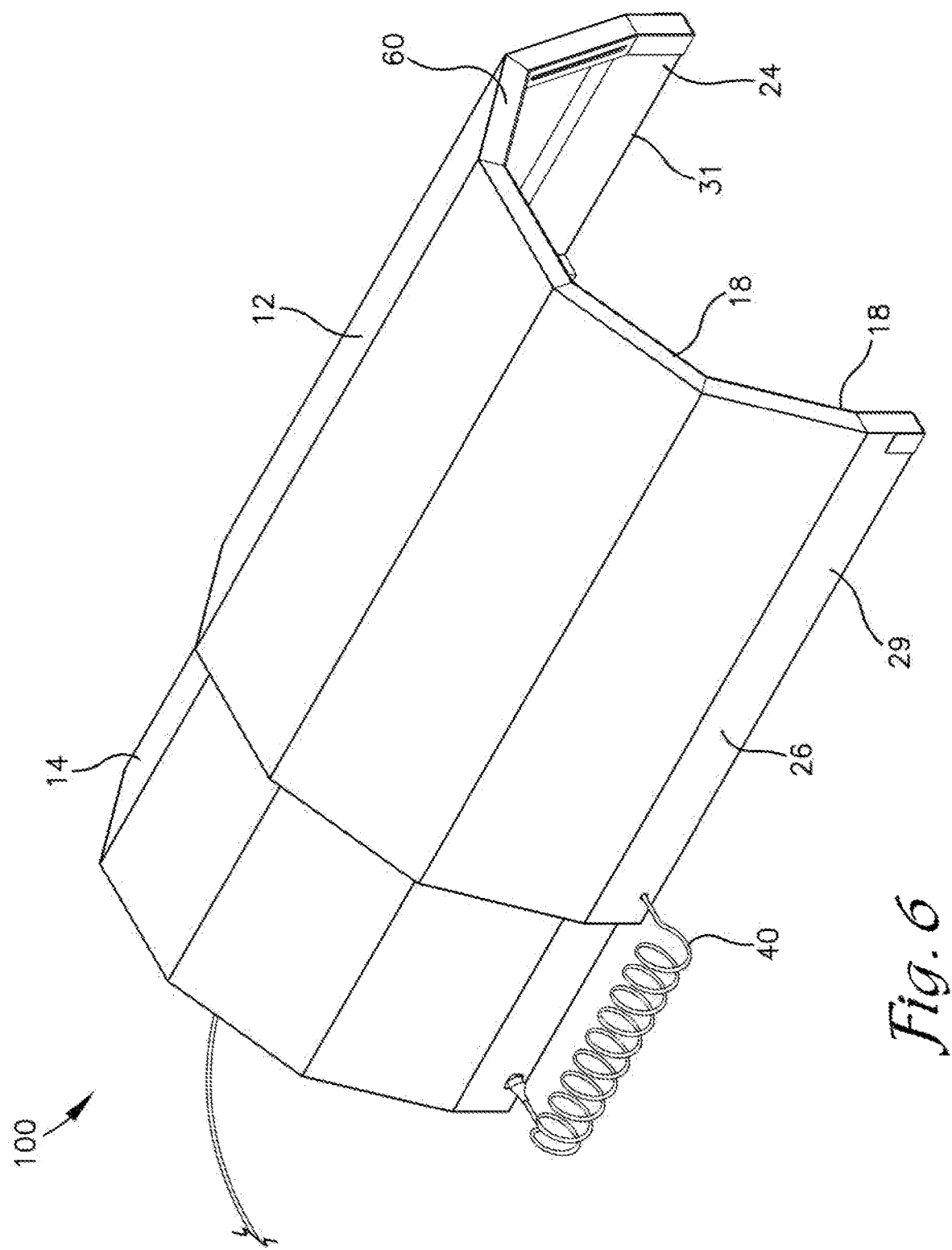
FIG. 6 is a perspective view of the personal therapy chamber of FIG. 3 depicted in accordance with an exemplary embodiment.

In the use configuration the upper unit 12 and the lower unit 14 each take on a generally half-cylindrical form. The form is referred to herein as being "cylindrical" for the sake of conciseness, however it is understood that the form is faceted and is more accurately described as partial tetradecagonal prism or partial 14-gon prism as shown in FIG. 3 or a partial hexadecagonal prism or partial 16-gon prism as depicted in FIGS. 6-7. Other configurations of the units 12, 14 with greater or fewer numbers of panels 18 forming a desired n-gonal prism may be employed. It is also understood that one or more of the panels 18 may be non-planar and thus not necessarily faceted; the resulting chamber 10 formed by the non-planar panels 18 may thus not be entirely faceted and may more closely approximate the form of a cylinder or truncated cone or may be some combination of faceted and non-faceted. Such variations are within the scope of the disclosure provided herein.

When in the use configuration, the lower unit 14 has a radial dimension that is slightly smaller than that of the upper unit 12 such that the lower unit 14 may be disposed at least partially within or overlapped by the upper unit 12. In one embodiment, the upper and lower units 12, 14 may not overlap and may be abutted end-to-end. The lower unit 14 may include an endwall 30 that encloses a distal end thereof and may include one or more additional emitters 28.

Figure 5:
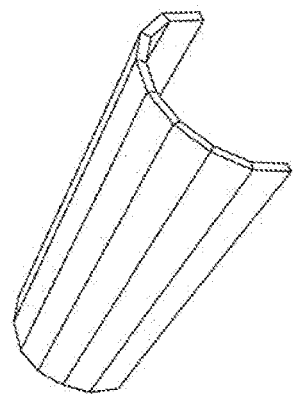
FIG. 5 is a perspective view of a personal therapy chamber formed from a single unit like that shown in FIG. 2 but with trapezoidal-shaped panels that provide a truncated-conical form when placed in a use configuration depicted in accordance with another exemplary embodiment.
Figure 4:
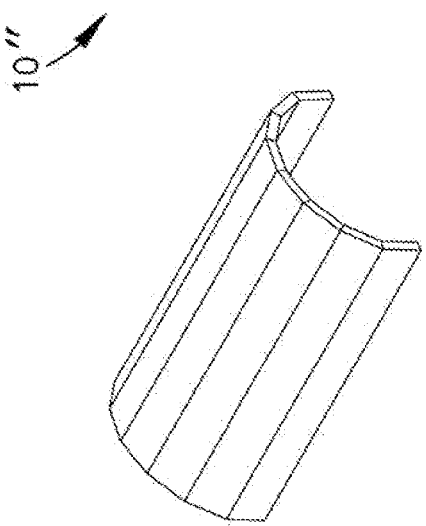
FIG. 4 is perspective view of a personal therapy chamber formed from a single, longer unit like that depicted in FIG. 2 depicted in accordance with another exemplary embodiment.

Although the therapy chamber 10 is described herein as including two units 12, 14 it is foreseen that more or fewer units may be employed without departing from the scope of this disclosure. For example, FIGS. 4 and 5 depict therapy units 10', and 10" comprised of a single unit. Further, although upper and lower units 12, 14 are described herein with a half- or semi-cylindrical form, it is understood that other forms, such as a conical form like that depicted in FIG. 5 can be employed in embodiments of the invention without departing from the scope described herein.

The length of the upper and lower units 12, 14 is generally equal and when placed end-to-end is sufficient to enclose the body of a user from the user's shoulders down, e.g. the user's head and at least a portion of the user's neck extend beyond a terminal end 60 of the upper unit 12 while the user's feet are in close proximity to the endwall 30.

The upper and lower units 12, 14 may be telescopically moveable relative to one another to adjust the overall length of the therapy chamber 10. As depicted in FIG. 14, a guide assembly that includes a guide 33 and a track 34 may be provided along adjacent surfaces of the upper and lower units 12, 14 to slideably couple the upper unit 12 with the lower unit 14 and to guide and/or aid relative translational movement of the units 12, 14 relative to one another. The guide 33 comprises an element such as a stud, flange, wheel, bearing, or the like configured to engage and move along the track 34. Alternatively, the upper and lower units 12, 14 may be separate units that can be employed independently. For example, a user may use only one of the upper or lower units 12, 14 when a full body therapy treatment is not desired. The user might alternatively employ the upper unit 12 in an upright, on-end position together with the lower unit 14 in the lying down position such that the user can sit upright with her torso substantially within the upper unit 12 and her legs extending beneath the lower unit 14.

One or more emitters 28 are coupled to or supported on or in the panel 18 and directed to emit radiation from the interior face 24 of the panel 18. In some embodiments, one or more of the panels 18 does not include an emitter 28. The emitters 28 may be disposed within an interior space of the frame member 20 or may be coupled to the interior face 24 of the panel 28. As depicted in FIG. 11, a single emitter 28 or single row of emitters may be disposed in each panel 18, or more than one row of emitters 28 may be disposed on each panel 28 as depicted in FIG. 12. The frame members may include a channel 41 extending transversely thereacross which provides a passageway in which wires, conductors, or other electrical couplings between the emitters 28 and/or the control unit 16 may be disposed.

The emitters 28 are preferably configured to emit in the infrared spectrum in one or more of the far-, mid-, and near-infrared bands, but may be configured to emit visible light and/or ultraviolet light instead of or in addition to infrared radiation. One or more emitters 28 may also be disposed on the endwall 30 of the lower unit 14 and/or on a pad 32 which may be provided for the user to lie on as described more fully below.

The emitters 28 preferably comprise planar elements like those described in U.S. Pat. No. 8,737,827 to Zack et al., the disclosure of which is hereby incorporated herein by reference. The emitters may also or alternatively comprise arrays of LEDs (light-emitting diodes) configured to emit near-infrared radiation and which may also emit in the visible light spectrum, e.g. red light. In another embodiment, the emitters 28 may comprise or include one or more other forms of heating elements including, for example, halogen bulbs, ceramic elements, and the like which emit in the near-, mid-, and/or far-infrared spectrums. As such, the user may be simultaneously provided with infrared radiation in one, two, or all three of the near-, mid-, and far-infrared spectrums.

Near-infrared is generally understood as the portion of the infrared spectrum having a wavelength between about 0.5 and about 1.5 micrometers or microns (μm) while mid-infrared is generally understood to comprise wavelengths between about 1.5 and about 7 μm and far-infrared generally comprises wavelengths between about 7 and about 1000 μm although the boundaries of these portions of the spectrum may vary by application.

The emitters 28 are preferably configured to produce no or very little electromagnetic field (EMF). In one embodiment, the emitters 28 produce EMF that is less than about 3 milliGauss (mG), or more preferably less than about 0.03 mG.

Sauna units and therapy chambers incorporating infrared heating elements and technology that may be employed in embodiments of the invention are described in greater detail in U.S. Pat. No. 8,588,593 to Zack et al. and U.S. Pat. No. 8,676,044 to O'Keefe et al., both of which are incorporated herein in their entirety by reference.

Each of the emitters 28 may be independently controllable or may be controlled as a group with one or more other emitters 28. Independent control of the emitters 28 may enable a user to tailor regions of the user's body that are targeted for application of the infrared radiation therapy. In some embodiments, one or more sensors may be employed to detect an overlap between the upper and lower units 12, 14, as depicted in FIG. 13. The control unit 16 may thus control one or more emitters 28 of the upper unit 12 within the overlap to reduce or halt emissions within the overlap.

A liner 31 may be disposed along the interior surfaces of each of the panels 18 of the upper and the lower units 12, 14. The liner 31 may be at least partially comprised of a fabric formed from CELLIANT infrared textiles and/or carbonized bamboo filaments alone or in combination with other fibers, among other fabrics, materials, and textiles.

Figure 19:
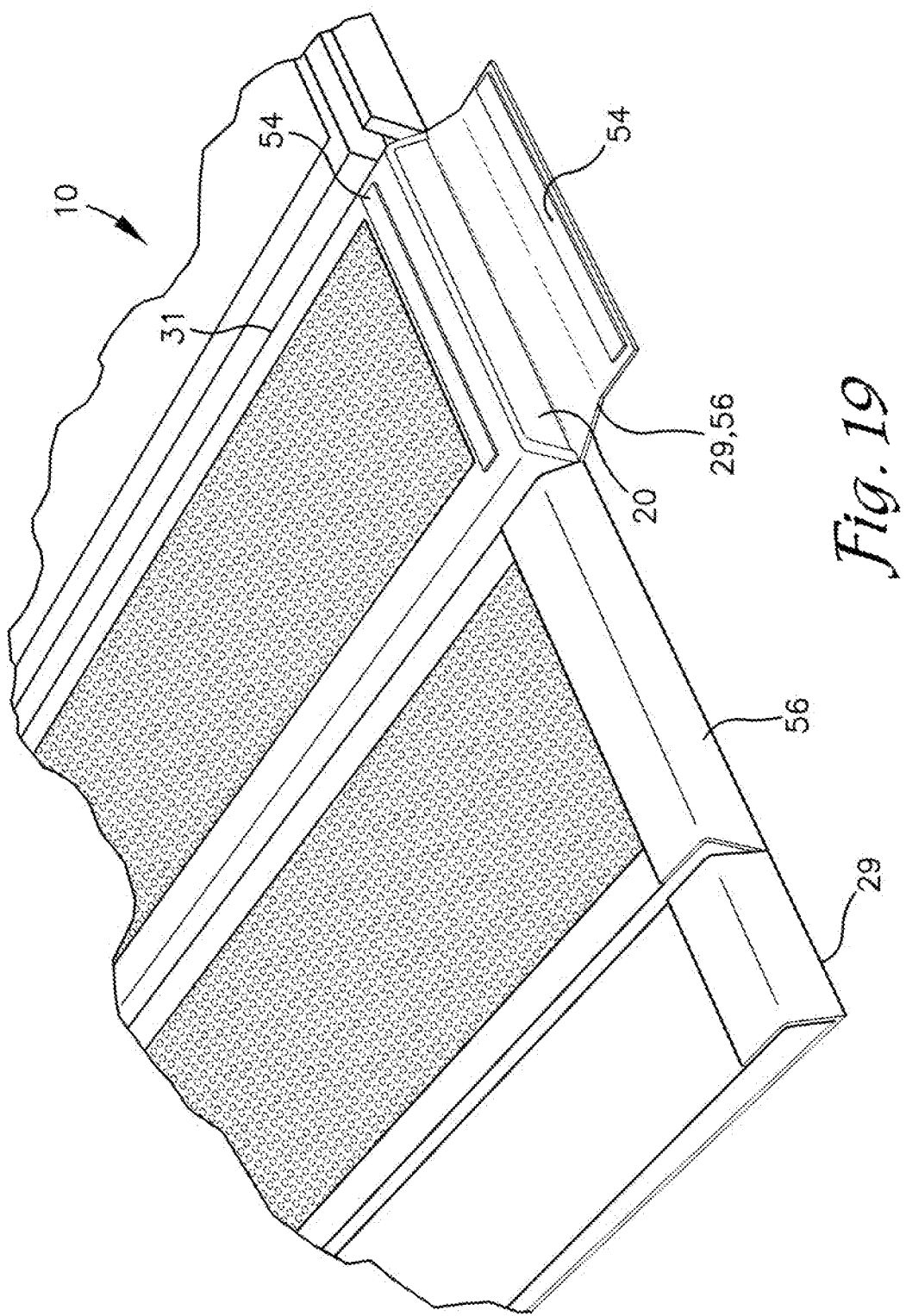
FIG. 19 is a perspective view of a unit of a portable therapy chamber depicting a pocket with a frame member and emitters disposed therein depicted in accordance with an exemplary embodiment.

With reference to FIG. 19, to construct the upper and lower units 12, 14, the sheet 29 forming the exterior surface of the units 12, 14 and the liner 31 forming the interior surface may be sewn or otherwise coupled together in appropriate locations to form a plurality of pockets 42 in which the frame members 20 can be inserted. Ends of the pockets 42 may also be sewn or otherwise closed off to retain the frame members 20 therein. In one embodiment, the pockets 42 employ one or more fasteners, such as hook-and-loop fasteners 54 applied to a flap 56 at the open end thereof that is useable to close off the end of the pocket 42 In another embodiment, the frame members 20 may be adhered or affixed to the sheet 29 and the liner 31 provided in sections that are adhered or affixed to interior faces of the frame members 20, among other configurations of the sheet 29 and liner 31 that may be employed.

A curtain 44 may be disposed near a terminal end 60 of the upper unit 12. The curtain 44 comprises one or more sections of a flexible material that extend across the distal end of the upper unit 12 to substantially enclose the opening formed thereby. In one embodiment, the curtain 44 is comprised of a fabric formed from CELLIANT infrared textiles and/or carbonized bamboo filaments alone or in combination with other natural and/or synthetic fibers. The curtain 44 may be configured to aid retention of heat produced by the emitters 28 within the interior of the therapy chamber 10. The curtain 44 also aids to enclose a gap between a user's body and the upper unit 12 when the user is positioned in the therapy chamber 10. The curtain 44 may be provided with a section of hook-and-loop fastener 46 that is mateable to a corresponding section of hook-and-loop fastener provided on an interior wall of the upper unit 12.

As depicted in FIGS. 16 and 18, a facial treatment emitter 48 such as a chromotherapy light unit, an infrared emitter, or the like may be disposed between the curtain and a terminal end 60 of each of the panels 18 of the upper unit 12. The facial treatment emitters 48 may comprise the same or different emitters as the emitters 28 described previously. In one embodiment, the facial treatment emitters 48 are provided within a recess 50 adjacent the distal end of the upper unit 12 and formed in the frame member 20.

Where the facial treatment emitters 48 are configured to emit visible light, they may be configured to selectively produce light within one of a plurality of predetermined colors or wavelength ranges and to enable selection and changing of the produced color by the user, e.g. the user can select and change between red, orange, yellow, green, blue, or violet. Or multiple colors might be selected and emitted simultaneously. In another embodiment, the facial treatment emitters 48 are configured to produce only a single predetermined color of light. The color and intensity may also be selectively emitted and varied based on one or more pre-programmed sequences. In one embodiment, the facial treatment emitters 48 are configured to emit infrared radiation in addition to light within the visible spectrum. For example, LEDs configured to emit in the near and/or mid-infrared spectrums can be integrated in the facial treatment emitters 48 or provided alongside the facial treatment emitters 48.

The facial treatment emitters 48 are positioned to direct the light produced thereby toward the face and or eyes of a user positioned within the therapy chamber 10 with her head extending from the upper unit 12 and adjacent to the facial treatment emitters 48. The user's face and eyes can thus be illuminated with a desired color of light to provide chromotherapy thereto. The chromotherapy may be provided during or simultaneously with a sauna session or independent of the operation of the emitters 28.

The control unit 16, like that depicted in FIG. 15 is communicatively coupled with the emitters 28 of each of the upper and lower units 12, 14 and provides one or more control surfaces that are useable to control operation thereof. The control unit 16 may be electrically coupled to the upper unit 12, the lower unit 14, the pad 32, and the facial treatment emitter 48 to provide power thereto and to control operations thereof. The control unit 16 receives power from an electrical coupling with a local power grid and distributes the power to each of the components of the therapy chamber 10.

The power grid is typically an alternating current (AC) power source. The control unit 16 may include one or more transformers and other components useable to transform AC to direct current (DC) and to provide voltages useable by the emitters 28 and any other emitters included in the therapy chamber 10. Conversion from AC to DC aids to reduce or eliminate electromagnetic fields produced by the emitters 28. Such AC to DC conversions take place within the control unit 16 and/or outside and separated from the upper and lower units 12, 14 so as to further eliminate or reduce potential exposure of the user to EMF. In another embodiment, AC power is employed directly by the heating elements without conversion to DC.

A wireless or wired remote control unit may be provided to enable the user to turn the emitters 28 on/off and/or to select a desired color of light, intensity, or other operational characteristic thereof. The remote control can be held in the hand of the user while inside the therapy chamber 10, thus eliminating any need for the user to exit the therapy chamber 10 to operate the therapy chamber 10 generally. The remote control may include tactile features that aid the user in identifying buttons and their functions by touch.

Wireless control may also be provided from a disparate source such as a networked computing device. To provide such functions, a wireless communications unit, such as a BLUETOOTH unit or WIFI unit may be included in the control unit 16. The BLUETOOTH and/or WIFI units may enable wireless operation/control of the therapy chamber 10 (including the emitters 28, among other functions) from a computing device such as a tablet computer, mobile device, smartphone, laptop computer, desktop computer, or the like. The BLUETOOTH unit may employ the wireless communication standards managed by the Bluetooth Special Interest Group, and/or may utilize other wireless communication standards, such as WiFi based on IEEE 802.11 standards, among others.

The pad 32 may be provided for placement on a surface beneath the therapy chamber 10. The pad 32 may comprise a generally planar component formed from a cushioning material, such as a foam, rubber, inflatable bladder(s), or the like. Preferably the pad 32 comprises a memory foam material. The pad 32 may include one or more outer layer materials that enclose the cushioning material, such as a material constructed at least partially from CELLIANT infrared textiles and/or carbonized bamboo fibers. The outer layer materials may provide antimicrobial properties and resistance to sweat or water, among other characteristics.

The pad 32 is divided into a plurality of sections that may be foldably joined together by, for example, living hinges to assist folding of the pad 32 for storage or transport. In another embodiment, the pad 32 is a single continuous section that can be rolled upon itself for storage/transport. The pad 32 preferably has a length sufficient to extend the full length of the upper and lower units 12, 14 placed end-to-end with the addition of a sufficient length to accommodate the user's head extending from the upper unit 12. The width of the pad 32 can extend beyond the outer perimeter of the upper and lower units 12, 14 or can be sized to fit within the perimeter.

In one embodiment, the pad 32 may be configured to form a storage wrap 38, as depicted in FIG. 7, within which the upper and lower units 12, 14 and any other components may be disposed when in the storage configuration. Handles or straps may be provided on a surface of the pad 32 to aid carrying of the components. In another embodiment, the pad 32 comprises a separate component from the storage wrap 38 which is comprised of one or more sections of a fabric or textile sized and configured to receive the components of the therapy chamber 10 for storage and transport.

A plurality of the emitters 28 are disposed within the body of the pad 32 to emit infrared radiation toward the user lying thereon. The pad 32 may include a pillow that is integrated with one of the sections thereof or that is included separately with the pad 32. The pillow, if separate from the pad 32, may be removably coupled to the pad 32, such as by hook-and-loop fasteners, buttons, snaps, or the like.

With continued reference to FIG. 7, operation of the therapy chamber 10 is described in accordance with an exemplary embodiment. From the storage orientation, a user first removes the upper and lower units 12, 14 from the storage wrap 38. When provided or desired, the pad 32 may be deployed on a surface such as a floor surface. The lower unit 14 and upper unit 12 may then be placed on the surface and unrolled or unfolded in the second direction (as described previously above) to the intermediate configuration.

Unfolding of the panels 18 of the upper and lower units 12, 14 may then continue in the second direction to move the side faces 22 thereof into abutment. Such may be completed by lifting each unit 12, 14 from a central location along its width and moving the longitudinal edges thereof toward one another and beneath the respective unit 12, 14, among other ways of achieving the use configuration of each of the units 12, 14. In embodiments in which the support member 52 is provided, the support member 52 is installed on the terminal end 60 of the upper unit 12. The support member 52 may be slideably engaged with the upper unit 12 with ends of the support member 52 at least partially encircling lateral edges of the upper unit 12 and the body of the support member 52 being placed in abutment with an interior wall of the upper unit 12. Additional engagements may also be provided between the support member 52 and the interior wall of the upper unit 12. As depicted in FIG. 18, apertures 58 may be provided in the support member 52 and may be aligned with facial treatment emitters 48 to enable the emitters 48 to emit through the apertures 58.

The upper and lower units 12, 14 are moved into longitudinal alignment and may be moved into an overlapping, telescoping configuration. When provided, the guide 33 and track 34 of the upper and lower units 12, 14 may also be engaged to aid alignment of the upper and lower units 12, 14 and relative translational movements therebetween. The endwall 30 may be engaged with a terminal end of the lower unit 14 via one or more engagements, fasteners, or the like. For example, the endwall 30 may be coupled to an interior face of the lower unit 14 or to the terminal end of the lower unit 14 via one or more sections of hook-and-loop fasteners. The endwall 30 may aid to support and retain the lower unit 14 in the use configuration.

An extensible cord 40 may be coupled between the upper and lower units 12, 14 to provide electrical communication therebetween and with the control unit 16. Cords or other electrical connections may also be coupled between the endwall 30, the pad 32, and the control unit 16. The control unit 16 is coupled to a power grid or other power source to receive electrical power therefrom.

The user selects a desired therapy profile, e.g. zones or groups of emitters 28, intensity, duration, etc. using the control unit 16. One or more preprogrammed therapy cycles might be provided by the control unit 16 and may be selectable by the user. For example, therapy cycles might be preprogrammed into the control unit 16 by the user or during manufacturing. The control unit 16 might also be configured to provide a dynamic therapy experience in which biological data is collected from the user and employed to select or adjust therapy cycles. For example, the user might wear a heart rate monitor that allows the control unit 16 to adjust a therapy cycle based on the user's heart rate.

The user may enter the therapy chamber 10 by sitting on the pad 32 and inserting her legs into the lower unit 14. The user might next lie down on the pad 32 and manually telescopically extend the upper unit 12 from its position overlapping the lower unit 14 toward her head and over her torso. The upper and lower units 12, 14 are lightweight so as to be easily moveable by the user. As a result, the user is enclosed between the pad 32 and the upper and lower units 12,14 with her head and neck extending through the curtain and outside of the upper unit 12. The user can thus remain enclosed within the therapy chamber 10 for the duration of her desired therapy treatment.

The user may also initiate a chromotherapy treatment simultaneously with her sauna treatment or without energizing the emitters 28. The facial therapy emitters 48 may be initiated and controlled via the control unit 16 and/or via a remote control which the user can keep in hand while within the therapy chamber 10. The user is preferably able to select a desired light color or colors to be emitted by the facial therapy emitter. The user may also be provided with the option to select one or more illumination sequences which may include various color changing sequences, light pulsing sequences, and/or light dimming sequences or options, among other lighting characteristics.

Many different arrangements of the various components depicted, as well as components not shown, are possible without departing from the scope of the claims below. Embodiments of the technology have been described with the intent to be illustrative rather than restrictive. Alternative embodiments will become apparent to readers of this disclosure after and because of reading it. Alternative means of implementing the aforementioned can be completed without departing from the scope of the claims below. Identification of structures as being configured to perform a particular function in this disclosure and in the claims below is intended to be inclusive of structures and arrangements or designs thereof that are within the scope of this disclosure and readily identifiable by one of skill in the art and that can perform the particular function in a similar way. Certain features and sub-combinations are of utility and may be employed without reference to other features and sub-combinations and are contemplated within the scope of the claims.

What is claimed is:

1. A personal therapy chamber comprising:
    a personal therapy unit that includes a plurality of elongate, substantially planar panels disposed side-by-side, one or more of the panels supporting an emitter configured to emit infrared radiation in one or more of a near- mid-, and far-infrared band; and
    a hinge coupling longitudinal edges of adjacent ones of the panels, the hinge enabling pivoting of each panel in both a first direction and a second direction relative to the adjacent panels, pivoting in the first direction moving the plurality of panels toward and into a storage configuration in which the plurality of panels are at least partially folded onto one another, pivoting in the second direction moving the plurality of panels toward and into a use configuration in which the longitudinal edges of the adjacent ones of the panels abut to limit an extent of pivoting in the second direction and provide the plurality of panels in an arched formation, the plurality of panels in the use configuration being disposed on a surface to form a chamber having an interior radial dimension sized to receive a torso of a human user with a head of the user extending at least partially beyond an end of the personal therapy unit.

2. The personal therapy chamber of claim 1 wherein the personal therapy unit comprises an upper unit, the personal therapy chamber further comprising:
    a lower unit comprised of a second plurality of elongate, substantially planar panels configured similarly to the upper unit, in the use configuration the lower unit being disposed in longitudinal alignment with the upper unit and being telescopically moveable relative to the upper unit.

3. The personal therapy chamber of claim 2, further comprising:
    a controller configured to control operation of each of the emitters in the upper unit and the lower unit, to detect an overlap between the upper unit and the lower unit, and to adjust one or more of the emitters within the overlap to reduce or eliminate heating of an exterior surface of one of the upper unit and the lower unit within the overlap.

4. The personal therapy chamber of claim 1, wherein the hinge is provided by a sheet material disposed to extend between exterior faces of adjacent ones of the panels.

5. The personal therapy chamber of claim 4, wherein the sheet material is a textile.

6. The personal therapy chamber of claim 1, wherein each of the panels in the plurality is disposed in a pocket formed by a sheet that is positioned on an exterior face of the panels and a liner that is disposed on an interior face of the panels, the pockets having an open longitudinal end through which the panels are inserted and a closure flap configured to close off the longitudinal end and retain the respective panel therein.

7. The personal therapy chamber of claim 1, further comprising:
    a support member having an arcuate form that mimics the arched formation of the personal therapy unit in the use configuration and that is engagable with the personal therapy unit in the use configuration, the support member aiding retention of the plurality of panels in the use configuration.

8. The personal therapy chamber of claim 7, wherein ends of the support member are configured to engage outermost longitudinal edges of the personal therapy unit.

9. The personal therapy chamber of claim 1, wherein each panel includes a frame that outlines a perimeter of the panel and supports the emitter, the frame having a side face along each longitudinal edge of the panel, the side faces being configured to abut side faces of the adjacent panels when in the use configuration, the side faces of each panel extending at an acute angle relative to a plane extending across an exterior face of each panel such that when the side faces of the adjacent panels are positioned in abutting relationship, the planes extending across the exterior face of each adjacent abutting panel extend at an acute angle relative to one another.

10. The personal therapy chamber of claim 9, wherein the side faces include one or more releasable retention elements that aid to maintain abutment of the side faces of the adjacent panels in the use configuration.

11. The personal therapy chamber of claim 9, further comprising:
    a recess in the frame adjacent a terminal end of the respective panel; and
    a second emitter disposed in the recess and configured to emit one or more of visible light and infrared radiation in one or more of the near-, mid-, and far-infrared radiation bands.

12. The personal therapy chamber of claim 9, further comprising:
    a channel formed in the frame and extending at least partially along a transverse dimension of a respective panel, the channel being configured to house one or more electrical conductors, the electrical conductors electrically coupling one or more of the emitters with a controller.

13. The personal therapy chamber of claim 1, further comprising:
a controller configured to control operation of each of the emitters in response to commands received from a user, the commands being received via wired or wireless communications.

14. The personal therapy chamber of claim 1, further comprising:
a pad that is disposable on a surface beneath the plurality of panels in the use configuration, the pad being reconfigurable to form a storage wrap within which the plurality of panels in the storage configuration fit.

15. The personal therapy chamber of claim 14, wherein the pad includes one or more infrared emitters configured to emit infrared radiation in one or more of the near-, mid-, and far-infrared radiation bands.

16. The personal therapy chamber of claim 1, further comprising:
a curtain coupled to an interior surface of the personal therapy unit adjacent the terminal end thereof, the curtain enclosing a space between a body of the user and the interior surface of the personal therapy unit.

17. A personal therapy chamber comprising:
an upper unit and a lower unit that each includes a plurality of elongate, substantially planar panels disposed side-by-side, each of the panels supporting an emitter configured to emit infrared radiation in one or more of a near-, mid-, and far-infrared band; and
a hinge coupling longitudinal edges of adjacent ones of the panels, the hinge enabling pivoting of each panel in both a first direction and a second direction relative to the adjacent panels, pivoting in the first direction moving the plurality of panels toward and into a storage configuration in which the plurality of panels are at least partially folded onto one another, pivoting in the second direction moving the plurality of panels toward and into a use configuration in which the longitudinal edges of the adjacent ones of the panels abut to limit an extent of pivoting in the second direction and provide the plurality of panels in an arched formation that is disposable on a surface, the upper unit and the lower unit being disposed on the surface in longitudinal alignment with the lower unit extending outward from a first end of the upper unit to form a chamber in which a human user is received with a head of the user extending at least partially beyond a second end of the upper unit and a remainder of the user's body being within the chamber.

18. The personal therapy chamber of claim 17, wherein the hinge is provided by a sheet material disposed to extend between exterior faces of adjacent ones of the panels.

19. The personal therapy chamber of claim 17, wherein each panel includes a frame that outlines a perimeter of the panel and supports the emitter, the frame having a side face along each longitudinal edge of the panel, the side faces being configured to abut side faces of the adjacent panels when in the use configuration, the side faces of each panel extending at an acute angle relative to a plane extending across an exterior face of each panel such that when the side faces of the adjacent panels are positioned in abutting relationship, the planes extending across the exterior face of each adjacent abutting panel extend at an acute angle relative to one another.

20. The personal therapy chamber of claim 17, further comprising:
a second emitter disposed in one or more of the plurality of panels of the upper unit adjacent the second end thereof, the second emitters configured to emit one or more of visible light and infrared radiation in one or more of the near-, mid-, and far-infrared radiation bands.

* * * * *